United States Patent
Karavas

(10) Patent No.: US 10,328,076 B2
(45) Date of Patent: Jun. 25, 2019

(54) PHARMACEUTICAL COMPOSITION COMPRISING A TRIAZOLE ANTIFUNGAL AGENT AND METHOD FOR PREPARATION THEREOF

(71) Applicant: PHARMATHEN S.A., Pallini-Attikis (GR)

(72) Inventor: Evangelos Karavas, Pallini Attikis (GR)

(73) Assignee: PHARMATHEN S.A., Pallini, Attikis (GR)

( * ) Notice: Subject to any disclaimer, the term of this patent is extended or adjusted under 35 U.S.C. 154(b) by 0 days.

(21) Appl. No.: 15/316,899

(22) PCT Filed: Jun. 9, 2015

(86) PCT No.: PCT/EP2015/001151
§ 371 (c)(1),
(2) Date: Dec. 7, 2016

(87) PCT Pub. No.: WO2015/188927
PCT Pub. Date: Dec. 17, 2015

(65) Prior Publication Data
US 2017/0095477 A1    Apr. 6, 2017

(30) Foreign Application Priority Data
Jun. 12, 2014  (GR) .............................. 20140100334

(51) Int. Cl.
*A61K 31/506* (2006.01)
*A61K 9/20* (2006.01)
*A61K 9/00* (2006.01)
*A61K 9/28* (2006.01)

(52) U.S. Cl.
CPC .......... *A61K 31/506* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2095* (2013.01); *A61K 9/2846* (2013.01); *A61K 9/2893* (2013.01)

(58) Field of Classification Search
CPC ............................ A61K 31/506; A61K 9/0053
USPC ......................................................... 514/256
See application file for complete search history.

(56) References Cited

U.S. PATENT DOCUMENTS

| | | |
|---|---|---|
| 2010/0086597 A1 | 4/2010 | Woo et al. |
| 2011/0028456 A1* | 2/2011 | Lulla ............... A61K 9/146 514/220 |

FOREIGN PATENT DOCUMENTS

| | | | |
|---|---|---|---|
| EP | 2596783 A1 | 5/2013 | |
| JP | 2004002245 A * | 1/2004 | |
| WO | 2009/012791 A1 | 1/2009 | |
| WO | WO 2009012791 A1 * | 1/2009 | ........... A61K 9/2009 |
| WO | 2010/084505 A2 | 7/2010 | |
| WO | WO 2010084505 A2 * | 7/2010 | ........... A61K 9/0014 |

OTHER PUBLICATIONS

Bhadiyadra et al, ePoster Library of AAPS (2014).*
Evonik Industries, "Aerosil and Aeroperl Colloidal Silicon Dioxide for Pharmaceuticals, Technical Information T1 1281," Aerosil.com (Jul. 2015), pp. 1-24. (Year: 2015).*
Database WPI Week 200410, Thomson Scientific, London, GB, AN 2004-094168, XP002743585, & JP 2004002245 A, Jan. 8, 2004, Abstract.
Written Opinion of the ISR, WIPO,PCT/EP2015/001151.

* cited by examiner

*Primary Examiner* — Craig D Ricci
*Assistant Examiner* — Janet L. Coppins
(74) *Attorney, Agent, or Firm* — AKC Patents, LLC

(57) ABSTRACT

The present invention relates to a stable pharmaceutical formulation of solid dosage forms for oral administration comprising a therapeutically effective amount of a triazole antifungal agent or pharmaceutical acceptable salt thereof, in particular Voriconazole and an effective amount of a solubility enhancing agent. It also relates to a process for the preparation thereof.

6 Claims, No Drawings

US 10,328,076 B2

PHARMACEUTICAL COMPOSITION COMPRISING A TRIAZOLE ANTIFUNGAL AGENT AND METHOD FOR PREPARATION THEREOF

TECHNICAL FIELD OF THE INVENTION

The present invention relates to a stable pharmaceutical formulation for oral administration containing a therapeutically effective quantity of a triazole antifungal agent such as Voriconazole or pharmaceutical acceptable salt thereof and a method for the preparation thereof.

BACKGROUND OF THE INVENTION

Voriconazole is a broad spectrum, triazole antifungal agent that is generally used to treat serious, invasive fungal infections including invasive aspergillosis, esophageal candidiasis, and infections caused by *Scedosporium apiospermum* (asexual form of *Pseudallescheria boydii*) and *Fusarium* spp. including *Fusarium solani*.

Like the other triazole antifungals, Voriconazole exerts its antifungal activity by inhibition of 14-alpha-lanosterol demethylation, which is mediated by fungal cytochrome P450 enzymes. This inhibition is more selective for fungal than for mammalian enzyme systems. The accumulation of 14-alphamethyl sterols results in a decrease in ergosterol, which is an essential component of fungal cell wall formation.

First generation triazole agents, such as fluconazole and itraconazole, have revolutionised the treatment of serious fungal infections. However, neither was an ideal agent. Itraconazole was plagued by absorption problems; fluconazole had a limited spectrum of antifungal activity and resistance was soon noted in immunosuppressed hosts who received long-term treatment. Voriconazole is a second generation triazole agent. Replacement of one of the triazole rings with a fluorinated pyrimidine and the addition of an α-methyl group resulted in expanded activity, compared with that of fluconazole and itraconazole.

The chemical name of Voriconazole is (2R,3S)-2-(2,4-difluorophenyl)-3-(5-fluoropyrimidin-4-yl)-1-(1H-1,2,4-triazol-1-yl)butan-2-ol and its molecular formula is $C_{16}H_{14}F_3N_5O$ corresponding to a molecular weight of 349.31. It is a white to almost white powder. It is very slightly soluble in water and freely soluble in acetone and dichlorometane.

U.S. Pat. No. 5,962,522 B discloses a method for increasing bioavailability of an orally administered pharmaceutical compound comprising orally co-administering Voriconazole and propyl gallate.

EP 1753402 B1 discloses a composition comprising Voriconazole and hydroxypropyl methyl cellulose acetate to improve physical stability.

WO 2006/084174 A2 discloses a composition comprising a molecular complex formed between Voriconazole and at least one agent selected from the group consisting of a hydroxy acid, a polyhydroxy acid, a related acid, a lactone form of these acids, and mixtures thereof to provide improved bioavailability.

Although each of the patents above represents an attempt to provide stable Voriconazole compositions for oral administration, there still remains the need in the art for alternative formulations with enhanced dissolution and adequate chemical and physical characteristics.

SUMMARY OF THE INVENTION

It is, therefore, an object of the present invention to provide a thermodynamically stable and efficient product comprising a triazole antifungal agent such as Voriconazole or pharmaceutical acceptable salt thereof suitable for oral administration.

The present invention aims at developing a formulation that not only matches the physical and chemical attributes of the reference product but also overcomes the disadvantages associated with the prior art compositions.

It is another object of the present invention to provide a stable solid dosage formulation for oral administration containing Voriconazole that overcomes the low water solubility of the active ingredient and has acceptable pharmacotechnical properties.

Further object of the present invention is to provide a film-coated tablet comprising Voriconazole or pharmaceutical acceptable salt thereof as an active ingredient, which is bioavailable and with sufficient self-life.

A major object of the present invention is the selection of the optimal combination of pharmaceutical acceptable excipients and method of preparation in order to achieve the appropriate dissolution profile and stability for the finished dosage form. Said dosage form affords predictable and reproducible drug release rates in order to achieve better treatment to a patient.

A further approach of the present invention is to provide a tablet composition for oral administration comprising Voriconazole which is manufactured through a fast, simple and cost-effective process.

According to another embodiment of the present invention, a process for the preparation of a stable, solid dosage form for oral administration, containing a triazole antifungal agent and in particular Voriconazole or pharmaceutical acceptable salt thereof as an active ingredient and an effective amount of a solubility enhancing agent is provided, which comprises the following steps:

Dissolving povidone in water;
Blending the active ingredient with the rest of the excipients of internal phase;
Kneading with povidone solution;
Drying the wetted mass;
Sizing the granules;
Adding at least one lubricant and mixing until uniformity is achieved;
Compressing the resulted mixture into a tablet dosage form;
Optionally applying a film-coating on the core.

Other objects and advantages of the present invention will become apparent to those skilled in the art in view of the following detailed description.

DETAILED DESCRIPTION OF THE INVENTION

For the purposes of the present invention, a pharmaceutical composition comprising an active ingredient is considered to be "stable" if said ingredient degrades less or more slowly than it does on its own and/or in known pharmaceutical compositions.

As already mentioned the main object of the present invention is to provide a stable pharmaceutical composition of Voriconazole or pharmaceutical acceptable salt thereof for oral administration that is simple to manufacture, bioavailable, cost effective and possesses good pharmacotechnical properties.

A very important parameter for the pharmaceutical industry is the achievement of linearity between the strength and the formulation. The present invention provides solid dosage forms that exhibit linearity between the strength of the drug formulation and the total mass of the formulation, by proportional increase of the amounts of the drug substance and the excipients in the formulation.

Particle size is having a pronounced effect on the absorption of drugs with low aqueous solubility. Due to the poor solubility of Voriconazole the influence of its particle size distribution on its dissolution was extensively studied in order to achieve the objects of the present invention.

In order for a drug to have its effect after oral administration it must go into solution and then diffuse through the gut wall into the body. The first step in that process is the disintegration of the dosage form followed by dissolution of the active ingredient. One way to increase dissolution rate of poorly soluble drugs such as Voriconazole is to increase the surface available for dissolution by reducing particle size. It has been surprisingly found that the objects of the present invention are achieved when the formulation is prepared using Voriconazole with specific particle size, in particular wherein $D_{90} < 100$ µm.

The bioavailability of poorly soluble drugs, for example Voriconazole, may be increased by using specific excipients able to enhance the active ingredient's solubility. Colloidal silicon dioxide when used in certain quantity provides enhanced dissolution of the composition. Moreover, such property of colloidal silicon dioxide is further intensified when it is used in the internal phase of the composition.

The "internal phase excipients" are desired to be intimately mixed with the active ingredient, such as inside a granule. On the other hand, the excipients that are desired not to be intimately mixed with the active ingredient are the "external phase excipients" and sit in the composition but outside the internal phase, which may be a granule.

Colloidal silicon dioxide is considered to have beneficial effect on the erodibility characteristics of the formulation promoting the disintegration of tablets. It contributes in API gelling, emulsification and consequently in API dissolution enhancement. Silicon dioxide is a hygroscopic material that may absorb large quantities of water. Due to its small particle size and large specific surface area it covers almost every particle of the API and during disintegration allows water to get into the tablet and decompose it.

Consequently, the small particle size of the active ingredient in combination with the use of colloidal silicon dioxide enhance Voriconazole's solubility and improve the dissolution properties of the tablets.

More particularly, the aim of the present invention is achieved when specific amount of colloidal silicon dioxide is incorporated in the internal phase of the composition. Therefore, the preferred composition of the present invention comprises 2% to 10% (w/w) of colloidal silicon dioxide, preferably 2% to 5% (w/w) and most preferably 4% of colloidal silicon dioxide.

The pharmaceutical compositions of the present invention may also contain one or more additional formulation excipients such as diluents, disintegrants, binders, lubricants, provided that they are compatible with the active ingredient of the composition, so that they do not interfere with it in the composition and in order to increase the stability of the drug and the self-life of the pharmaceutical product.

Diluents increase the bulk of a solid pharmaceutical composition, and may make a pharmaceutical dosage form easier for the patient and care giver to handle. Diluents for solid compositions include, for example, microcrystalline cellulose, dextrose, fructose, mannitol, sorbitol, pregelatinized starch, sucrose, xylitol, maltose, maltodextrin, maltitol, lactose.

The dissolution rate of a compacted solid pharmaceutical composition in the patient's stomach may be increased by the addition of a disintegrant to the composition. Disintegrants include sodium starch glycolate, alginic acid, carboxymethylcellulose sodium, croscarmelose sodium, guar gum, methylcellulose, sodium alginate.

Solid pharmaceutical compositions that are compacted into a dosage form, such as a tablet, may include excipients whose function include helping to bind the active ingredient and other excipients together after compression. Binders for solid pharmaceutical compositions include carbomer, ethyl cellulose, gelatin, guar gum, hydroxyethyl cellulose, methylcellulose, polydextrose, polyethylene oxide, povidone.

When a dosage form such as a tablet is made by the compaction of a powdered composition, the composition is subjected to pressure from a punch and dye. Some excipients and active ingredients have a tendency to adhere to the surfaces of the punch and dye, which can cause surface irregularities to the product. A lubricant can be added to the composition to reduce adhesion and ease the release of the product from the dye. Lubricants include talc, magnesium stearate, calcium stearate, glyceryl behenate, hydrogenated castor oil, stearic acid, sodium lauryl sulphate.

The tablets of the present invention may be optionally film-coated with an immediate release coating preparation such as Opadry® in order to obtain tablets with smooth surface. The film-coating is prepared by dissolving the coating composition in water and/or organic solvent and then is sprayed on the tablet core. The coating process is commonly performed in a coating pan.

The following examples illustrate preferred embodiments in accordance with the present invention without limiting the scope or spirit of the invention.

EXAMPLES

Example 1

TABLE 1

Compositions 1 to 4 of example 1

| | Composition | | | |
|---|---|---|---|---|
| | 1 | 2 | 3 | 4 |
| | % w/w | | | |
| Internal phase | | | | |
| Voriconazole | 33.33 | 33.33 | 33.33 | 33.33 |
| Pregelatinized starch | 19.39 | 19.39 | 18.39 | 18.39 |
| Lactose monohydrate | 42.28 | 41.28 | 41.28 | 39.28 |
| Povidone | 2.00 | 3.00 | 3.00 | 3.00 |
| Croscarmellose sodium | 2.00 | 2.00 | 3.00 | 3.00 |
| External phase | | | | |
| Magnesium stearate | 1.00 | 1.00 | 1.00 | 1.00 |
| Croscarmellose sodium | — | — | — | 2.00 |
| | 100 | | | |

Composition 1 was manufactured with three different processes, i.e. dry mixing, wet granulation using as solvent ethanol and wet granulation using as solvent water.

Composition 1 was first manufactured with a dry mixing procedure comprising the following steps:

Voriconazole was blended with excipients of internal phase;

Magnesium stearate was added to the mixture;

The resulted mixture was compressed into tablet dosage form.

The physicochemical characteristics achieved are presented in the following table:

TABLE 2

Results of Composition 1 manufactured with dry mixing

| TEST PARAMETERS | Results |
|---|---|
| Carr's Index | 44.5% |
| Hardness | 71 N |
| Disintegration time | 0'47"-1'00" |

Composition 1 was also manufactured with wet granulation process using as solvent ethanol according to the following steps:
Voriconazole was blended with excipients of internal phase;
The granulation liquid, ethanol, was added to the mixture;
The wetted mass was dried;
Magnesium stearate was added to the mixture;
The resulted mixture was compressed into tablet dosage form.

The physicochemical characteristics achieved are presented in table 3 below:

TABLE 3

Results of Composition 1 manufactured with wet granulation and using ethanol as solvent

| TEST PARAMETERS | Results |
|---|---|
| Carr's Index | 31.0% |
| Hardness | 100 N |
| Disintegration time | 7'28"-8'44" |

Finally, Composition 1 was manufactured with wet granulation process using as solvent water according to the following steps:
Voriconazole was blended with excipients of internal phase;
The granulation liquid, water, was added to the mixture;
The wetted mass was dried;
Magnesium stearate was added to the mixture;
The resulted mixture was compressed into tablet dosage form.

The physicochemical characteristics achieved are presented in table 4 below:

TABLE 4

Results of Composition 1 manufactured with wet granulation and using water as solvent

| TEST PARAMETERS | Results |
|---|---|
| Carr's Index | 28% |
| Hardness | 113 N |
| Disintegration time | 9'55"-11'38" |

Wet granulation was chosen for the development of Voriconazole tablets as compositions prepared with such process exhibited better compressibility and flow properties of the granule.

In order to improve hardness of Voriconazole tablets, in Composition 2 povidone was used in higher amount. Composition 2 was prepared with wet granulation process using water as solvent according to steps followed for the preparation of Composition 1.

The physicochemical characteristics achieved are presented in table 5 below:

TABLE 5

Results of Composition 2

| TEST PARAMETERS | Results |
|---|---|
| Carr's Index | 29% |
| Hardness | 125 N |
| Disintegration time | 13'15"-14'58" |

In order to improve disintegration time and enhance binding properties of povidone, in Composition 3 the amount of croscarmellose sodium was increased and povidone was dissolved in water and then was mixed with API and the rest of excipients.

Composition 3 was prepared according to the following manufacturing process:
Povidone was dissolved in water;
Voriconazole was blended with pregelatinized starch, lactose monohydrate and croscarmellose sodium;
The mixture was kneaded with povidone solution;
The wetted mass was dried;
The external phase was added to the mixture;
The resulted mixture was compressed into tablet dosage form.

The physicochemical characteristics achieved are presented in table 6 below:

TABLE 6

Results of Composition 3

| TEST PARAMETERS | Results |
|---|---|
| Carr's Index | 29% |
| Hardness | 145 N |
| Disintegration time | 9'15"-11'58" |

Dissolution profile of Composition 3 is presented below:

TABLE 7

Dissolution profile of Composition 3

| Time (min) | (% release) |
|---|---|
| 5 | 29.73 |
| 10 | 53.42 |
| 15 | 66.21 |
| 20 | 73.58 |
| 30 | 82.14 |
| 45 | 89.42 |

Although binding properties of povidone were improved and better hardness and lower friability were achieved, dissolution profile of Composition 3 was quite low.

Thus, in Composition 4 an extra quantity of croscarmellose sodium was employed to the external phase in order to improve the disintegration capability of the tablets produced since it plays important role to the dissolution rate of the active ingredient.

The applied manufacturing process remained the same as in Composition 3.

The physicochemical characteristics achieved are presented in table 8 below:

TABLE 8

Results of Composition 4

| TEST PARAMETERS | Results |
|---|---|
| Carr's Index | 25.4% |
| Hardness | 133 N |
| Disintegration time | 7'50"-8'25" |

Dissolution profile of Composition 4 is presented below:

TABLE 9

Dissolution profile of Composition 4

| Time (min) | (% release) |
|---|---|
| 5 | 21.02 |
| 10 | 44.37 |
| 15 | 63.22 |
| 20 | 74.58 |
| 30 | 86.81 |
| 45 | 96.81 |

Dissolution results were not satisfying even after the addition of extra quantity of the disintegrant in the external phase.

The low dissolution profile was attributed to Voriconazole's low aqueous solubility. Thus, API with lower particle size distribution compared to API of previous compositions was used in Composition 5. For the size reduction, API was subjected to milling process to achieve D90<100 μm.

Composition 5 was qualitatively and quantitatively identical to Composition 3 and was prepared with the same manufacturing process as Composition 3.

The physicochemical characteristics achieved are presented in table 10 below:

TABLE 10

Results of Composition 5

| TEST PARAMETERS | Results |
|---|---|
| Carr's Index | 17.9% |
| Hardness | 175 N |
| Disintegration time | 7'00"-7'20" |

Dissolution profile of Composition 5 is presented below:

TABLE 11

Dissolution profile of Composition 5

| Time (min) | (% release) |
|---|---|
| 5 | 42.58 |
| 10 | 79.63 |
| 15 | 90.07 |
| 20 | 94.97 |
| 30 | 93.47 |
| 45 | 94.00 |

Although dissolution profile was improved by incorporating API with lower particle size, there was further need to enhance dissolution. Therefore, it was decided to use colloidal silicon dioxide in the internal phase. In Compositions 6, 7, and 8 of example 2, 6%, 8% and 10% of colloidal silicon dioxide was used in internal phase respectively.

Example 2

TABLE 12

Compositions 6 to 8 of example 2

| | Composition | | |
|---|---|---|---|
| | 6 | 7 | 8 |
| | w/w % | | |
| Internal Phase | | | |
| Voriconazole | 33.33 | 33.33 | 33.33 |
| Pregelatinized starch | 16.89 | 16.89 | 16.89 |
| Lactose Monohydrate | 36.78 | 34.78 | 32.78 |
| Povidone | 3.00 | 3.00 | 3.00 |
| Croscarmellose sodium | 3.00 | 3.00 | 3.00 |
| Colloidal silicon dioxide | 6.00 | 8.00 | 10.00 |
| External Phase | | | |
| Magnesium stearate | 1.00 | 1.00 | 1.00 |
| Total | 100.00 | | |

TABLE 13

Results of Compositions 6 to 8

| | COMPOSITIONS | | |
|---|---|---|---|
| | 6 | 7 | 8 |
| TEST PARAMETERS | | Results | |
| Carr's Index | 18% | 16% | 16% |
| Hardness | 156 N | 160 N | 144 N |
| Disintegration time | 4'00"-4'20" | 2'35"-3'05" | 1'40"-2'50" |

TABLE 14

Dissolution profiles of Compositions 6 to 8

| | COMPOSITIONS | | |
|---|---|---|---|
| | 6 | 7 | 8 |
| Time (min) | | (% release) | |
| 5 | 49.10 | 56.78 | 67.44 |
| 10 | 88.10 | 85.26 | 90.95 |
| 15 | 95.90 | 96.12 | 98.56 |
| 20 | 97.20 | 99.73 | 101.01 |
| 30 | 98.10 | 102.11 | 103.06 |
| 45 | 98.60 | 103.06 | 103.86 |

According to the results, amount of colloidal silicon dioxide up to 10% enhances dissolution rate and extent of Voriconazole.

The preferred composition of the present invention is presented in table 15 below:

TABLE 15

Preferred composition of the present invention

| Ingredients | % w/w | mg per tablet | mg per tablet |
|---|---|---|---|
| Internal Phase | | | |
| Voriconazole | 33.33 | 50.00 | 200.00 |
| Pregelatinized starch | 16.89 | 25.33 | 101.32 |
| Lactose Monohydrate | 38.78 | 58.17 | 232.68 |
| Povidone | 3.00 | 4.50 | 18.00 |

TABLE 15-continued

Preferred composition of the present invention

| Ingredients | % w/w | mg per tablet | mg per tablet |
|---|---|---|---|
| Croscarmellose sodium | 3.00 | 4.50 | 18.00 |
| Colloidal silicon dioxide | 4.00 | 6.00 | 24.00 |
| External Phase | | | |
| Magnesium stearate | 1.00 | 1.50 | 6.00 |
| Total for uncoated | 100.00 | 150.00 | 600.00 |
| Coating | | | |
| Opadry II White OY-LS 28908 | 2.00 | 3.00 | 12.00 |

The preferred composition of the present invention was prepared according to the following manufacturing process:
Dissolving of povidone in water;
Blending Voriconazole with pregelatinized starch, lactose monohydrate, croscarmellose sodium and colloidal silicon dioxide;
Kneading with povidone solution;
Drying the wetted mass;
Sizing the granules;
Adding magnesium stearate to the mixture;
Compressing the obtained mixture into tablet dosage form;
Optionally, applying a film-coating on the core.

Stability data after 6 months under long term, intermediate and accelerated conditions as well as physical properties and dissolution rate of the active ingredient in the preferred composition of the present invention are presented in table 13 below:

TABLE 16

Results of preferred composition of the present invention

| | | Stability data after 6 months | | |
|---|---|---|---|---|
| Control Tests | Limits | 25° C./60% RH | 30° C./65% RH | 40° C./75% RH |
| Hardness | NLT 100 N | 242 N | 238 N | 233 N |
| Loss on Drying | NMT 6.0% | $7^{41}$-$10^{13}$ | $8^{33}$-$10^{47}$ | $7^{29}$-$9^{50}$ |
| Disintegration | NMT 30 min | 3.7% | 4.0% | 5.1% |
| Assay | 95.0-105.0% of the stated amount of Voriconazole | 102.0% | 99.8% | 99.7% |
| Dissolution | Apparatus II Paddles 50 rpm, Comply with the Ph.Eur current edition (introducing S1, S2) % Dissolved: Q = 75% at 45 min | 99.6% | 99.6% | 99.3% |
| Related Substances | Impurity A NMT 0.2% | 0.01% | 0.02% | 0.02% |
| | Impurity C NMT 0.2% | BQL | 0.01% | 0.03% |
| | Impurity J NMT 0.2% | ND | ND | ND |
| | Any Individual Unknown NMT 0.2% | RRT0.39: BQL | RRT0.39: BQL | RRT0.39: BQL |
| | Total NMT 2.0% | 0.02% | 0.04% | 0.06% |

From the results demonstrated above we can conclude that the preferred tablet composition of the present invention exhibits the desirable dissolution rate and extent, satisfactory physical properties as well as physical and chemical stability.

While the present invention has been described with respect to the particular embodiments, it will be apparent to those skilled in the art that various changes and modifications may be made in the invention without departing from the spirit and scope thereof, as defined in the appended claims.

The invention claimed is:

1. A solid pharmaceutical composition for oral administration comprising:
   Voriconazole or pharmaceutically acceptable salt thereof and an effective amount of colloidal silicon dioxide as a solubility enhancing agent;
   wherein the solid pharmaceutical composition comprises an internal phase and an external phase;
   wherein the internal phase comprises particles having a dimension less than 100 micrometers and wherein each particle of the internal phase comprises the colloidal silicon dioxide intimately mixed and incorporated with the Voriconazole; and
   wherein the external phase is located outside the internal phase and comprises excipients that are not intimately mixed with the Voriconazole; and
   wherein one of said excipients incorporated in the external phase comprises magnesium stearate.

2. The pharmaceutical composition according to claim 1, comprising colloidal silicon dioxide in an amount of from 2% to 10% (w/w).

3. The pharmaceutical composition according to claim 1, wherein it further comprises at least one pharmaceutically acceptable excipient selected from diluents, binders, disintegrants and lubricants.

4. A process for the preparation of a tablet composition comprising Voriconazole or pharmaceutically acceptable salt thereof and an effective amount of colloidal silicon dioxide as a solubility enhancing agent comprising the steps of:
- Dissolving of povidone in water;
- Blending Voriconazole with pregelatinized starch, lactose monohydrate, croscarmellose sodium and colloidal silicon dioxide;
- Kneading with povidone solution;
- Drying the wetted mass;
- Sizing the granules;
- Adding magnesium stearate to the mixture;
- Compressing the obtained mixture into tablet dosage form;
- Optionally, applying a film-coating on the core.

5. The process according to claim 4, wherein it comprises colloidal silicon dioxide in an amount of from 2% to 10% (w/w).

6. A tablet composition comprising Voriconazole or pharmaceutically acceptable salt thereof and an effective amount of colloidal silicon dioxide as a solubility enhancing agent and wherein the tablet is prepared by the process of claim 4; and
- wherein the tablet comprises an internal phase and an external phase;
- wherein the internal phase comprises particles having a dimension less than 100 micrometers and wherein each particle of the internal phase comprises the colloidal silicon dioxide intimately mixed and incorporated with the Voriconazole; and
- wherein the external phase is located outside the internal phase and comprises excipients that are not intimately mixed with the Voriconazole.

* * * * *